(12) United States Patent
Komulainen et al.

(10) Patent No.: US 6,504,617 B2
(45) Date of Patent: Jan. 7, 2003

(54) METHOD AND MEASURING ARRANGEMENT FOR MEASURING PAPER SURFACE

(75) Inventors: Hannu Komulainen, Sonkajärvi (FI); Jaana Hakkarainen, Lempäälä (FI); Keijo Lehmikangas, Puolanka (FI)

(73) Assignee: Metso Paper Automation Oy, Tampere (FI)

( * ) Notice: Subject to any disclaimer, the term of this patent is extended or adjusted under 35 U.S.C. 154(b) by 0 days.

(21) Appl. No.: 09/953,384

(22) Filed: Sep. 14, 2001

(65) Prior Publication Data

US 2002/0114494 A1 Aug. 22, 2002

Related U.S. Application Data

(63) Continuation of application No. PCT/FI00/00411, filed on May 9, 2000.

(30) Foreign Application Priority Data

May 10, 1999 (FI) .................................................. 991072

(51) Int. Cl.$^7$ ........................... C01N 21/57; C01B 11/30
(52) U.S. Cl. ....................................... 356/600; 356/446
(58) Field of Search ................................ 356/600, 445, 356/446, 447, 448

(56) References Cited

U.S. PATENT DOCUMENTS

| | | | |
|---|---|---|---|
| 3,922,093 A | 11/1975 | Dandliker et al. | |
| 4,806,018 A | 2/1989 | Falk | |
| 4,878,114 A | * 10/1989 | Huynh et al. | 358/106 |
| 5,162,660 A | * 11/1992 | Popil | 250/561 |
| 5,686,731 A | 11/1997 | Wiles et al. | |
| 5,689,757 A | * 11/1997 | Ferrante et al. | 356/446 |

FOREIGN PATENT DOCUMENTS

| | | |
|---|---|---|
| DE | 29 05 727 A1 | 11/1979 |
| DE | 30 20 044 A1 | 12/1981 |
| DE | 197 33 775 A1 | 2/1999 |
| GB | 2 037 978 A | 7/1980 |
| WO | WO 99/10730 | 3/1999 |

OTHER PUBLICATIONS

Copy of International Search Report for PCT/FI00/00411, completed Aug. 28, 2000.
Copy of Finnich Office Action for Patent Appl. No. 991072, dated Apr. 26, 2000.
Standard T 480 om–92; Specular Gloss Of Paper And Paperboard at 75 Degrees; TAPPI.
J. Steurer, H. Giebel, and W. Altner, Ein lichtmikroskopisches Verfahren zur zweieinhalbdimensionalen Auswertung von Oberflächen, In Proc. 8. DAGM–Symp. Mustererkennung, 1986, Informatik Fachberichte 125, edited by G. Hartmann, pp. 66–70, Springer, Berlin.

\* cited by examiner

Primary Examiner—Richard A. Rosenberger
(74) Attorney, Agent, or Firm—Alston & Bird LLP

(57) ABSTRACT

The invention relates to a method and a measuring arrangement for determining gloss of paper or paperboard. The paper or paperboard surface is illuminated with collimated light substantially parallel with the normal of the paper or paperboard surface. An image is produced from the paper or paperboard surface by means of reflected optical radiation. The reflected optical radiation is used for producing an image of the paper or paperboard surface onto the pixels of the camera's detector surface, each of the pixels imaging an area in the order of micrometers of the paper or paperboard surface. An aperture provided in front of the camera is used for adjusting the incidence angles of the reflected radiation, which affects the measurement of gloss. Gloss of paper or paperboard is measured on the basis of the intensity of the pixels on the camera's detector surface.

26 Claims, 7 Drawing Sheets

METHOD AND MEASURING ARRANGEMENT FOR MEASURING PAPER SURFACE

This application is a Continuation of International Application PCT/FI00/00411 filed on May 9, 2000, which designated the U.S. and was published under PCT Article 21(2) in English, and which is incorporated herein in its entirety by reference.

FIELD OF THE INVENTION

The solution according to the invention is used for measuring a surface property of paper or paperboard. The paper or paperboard surface is illuminated and the illuminated paper or paperboard surface is imaged by a camera for measuring.

BACKGROUND OF THE INVENTION

The properties used for describing the surface properties of paper and paperboard include roughness and gloss which are used e.g. for estimating the printability of paper. The probably most common way of measuring paper roughness is based on airflow measuring methods which are employed in the apparatuses of Bendtsen, Parker-Prit-Surf-Sheffield, Bekk and Gurley Hill, for example. In these solutions a cylindrical element is pressed against the paper or paperboard surface with a certain amount of force. A pressure difference with respect to the ambient air is caused in the element, and the air flowing through an opening between the edge of the cylindrical element and the paper or paperboard surface is measured. There are several problems related to these measurements. The parameter representing roughness is also influenced by the porosity of paper. The measurement is also integrally directed at a large surface area, for which reason accurate information on the detailed structure of the paper surface cannot be obtained. This is disadvantageous to the estimation of printability, for example. A further disadvantage is an error factor caused by the dependency between the measuring result and the force used for pressing the cylindrical element against the paper or paperboard surface.

The surface properties of paper and paperboard can also be measured optically. In profilometric roughness measurement the paper surface is examined unidimensionally using a focused ray in the same way as when reading a CD. Problems are caused by porosity, paper transparency and strong reflectance, if any, which distort the profile. Unidimensionality of the measurement is also a disadvantage. Roughness can also be measured utilizing light scattering. In the prior art solution the paper surface is conventionally illuminated at an oblique angle (45° to 85°) with respect to the normal of the surface, and the intensity distribution of radiation from the direction of specular reflection is measured to determine roughness. This solution is described in greater detail e.g. in Finnish publication no. 56453, which is incorporated herein by reference. Specular reflection is typically also measured in connection with the measurement of the gloss. In the standardized solution according to the prior art, gloss of paper or paperboard is measured by illuminating the paper or paperboard surface at a large angle (e.g. 75°) with respect to the surface normal and detecting optical radiation reflected from the surface at the angle of reflection. This solution is described more closely in standard T 480 om-92, which is incorporated herein by reference. The prior art measuring arrangements measure gloss and roughness integrally from a large area the size of which is usually dozens of square millimeters. The average measured from a large area does not give accurate information on the structure of the paper surface and thus e.g. printability cannot be estimated reliably. The large measuring angle further impairs the measuring accuracy. An additional problem is that the surface roughness and the surface gloss are mixed with each other and they cannot be determined separately with any certainty.

BRIEF DESCRIPTION OF THE INVENTION

An object of the invention is to provide a method and an apparatus implementing the method to eliminate the above-mentioned problems. This is achieved with the solution according to the invention which relates to a method of determining a surface property of paper or paperboard, the method comprising illuminating the paper or paperboard surface and imaging the illuminated paper or paperboard surface onto the pixels of a camera's detector surface. For measuring at least gloss as the micro surface property, the method according to the invention comprises illuminating the paper or paperboard surface with collimated light substantially parallel with the normal of the paper or paperboard surface; controlling the reflected optical radiation with an aperture of the desired size before the camera; producing an image of the paper or paperboard surface onto the pixels of the camera's detector surface by means of the reflected optical radiation, each of the pixels imaging an area in the order of micrometers of the paper or paperboard surface, and measuring at least the gloss of paper or paperboard surface on the basis of the intensity of the pixels on the camera's detector surface.

The invention also relates to a measuring arrangement for determining a surface property of paper or paperboard, the measuring arrangement comprising an optical power source for illuminating the paper or paperboard surface and a camera for imaging the illuminated paper or paperboard surface onto the pixels of the camera's detector surface. The measuring arrangement according to the invention comprises, for measuring at least one micro surface property, a collimating optical block for collimating the optical radiation emitted from the optical power source; a partially permeable mirror for projecting the optical radiation onto the paper or paperboard surface substantially parallel with the normal of the paper or paperboard surface; an imaging optical block for producing an image of the illuminated paper or paperboard surface onto the pixels of the camera's detector surface by means of the reflected optical radiation; an aperture of the desired size for controlling the reflected optical radiation; the measuring arrangement being arranged to measure at least gloss of the paper or paperboard surface on the basis of the intensity of the pixels on the camera's detector surface.

The dependent claims disclose the preferred embodiments of the invention.

The solution according to the invention is based on illuminating the paper or paperboard surface with collimated optical radiation from the direction of the surface normal. An aperture is used for controlling the quality of the micro surface property to be measured. When gloss is measured, the aperture is used for adjusting the direction of optical radiation entering the camera. When roughness is measured, the aperture is used for adjusting the depth of focus of the image formed onto the pixels of the camera's detector surface. In both cases the micro surface properties are measured by means of the intensity received by the pixels on the camera's detector surface.

The measuring arrangement and method according to the invention provide several advantages. The invention enables measuring of a surface property of paper or paperboard from a surface area in the order of micrometers, in which case the surface properties can be determined as micro surface properties. This allows to separate gloss and roughness reliably from each other. Thanks to this, the printability of paper or paperboard can be estimated accurately, which results in considerable savings in the production costs of various printed goods because paper or paperboard processing can be controlled during the manufacture. In practice this means that the consumption of ink used in printing, for example, can be optimized, which allows to guarantee good quality of the text and pictures.

BRIEF DESCRIPTION OF DRAWINGS

The invention will be described in greater detail by means of preferred embodiments, with reference to the accompanying drawings, in which.

DETAILED DESCRIPTION OF THE INVENTION

The measuring arrangement and method according to the invention are used for measuring a micro surface property of the paper or paperboard surface, which can be utilized in the estimation of printability of paper or paperboard. The micro surface property to be measured is gloss. The same measuring arrangement can also be used for measuring roughness.

The simplest way of separating gloss and roughness from each other is to think that roughness means larger irregularities on the surface to be measured than the irregularities affecting gloss. In optical measurement roughness is represented by irregularities which exceed the wavelength (considerably), whereas the irregularities affecting gloss are mainly in the range of the wavelength. This means that scattered optical radiation consists of rays reflected in different directions according to the surface profile and of rays diffracted from the small irregularities on the surface.

Figure 1:
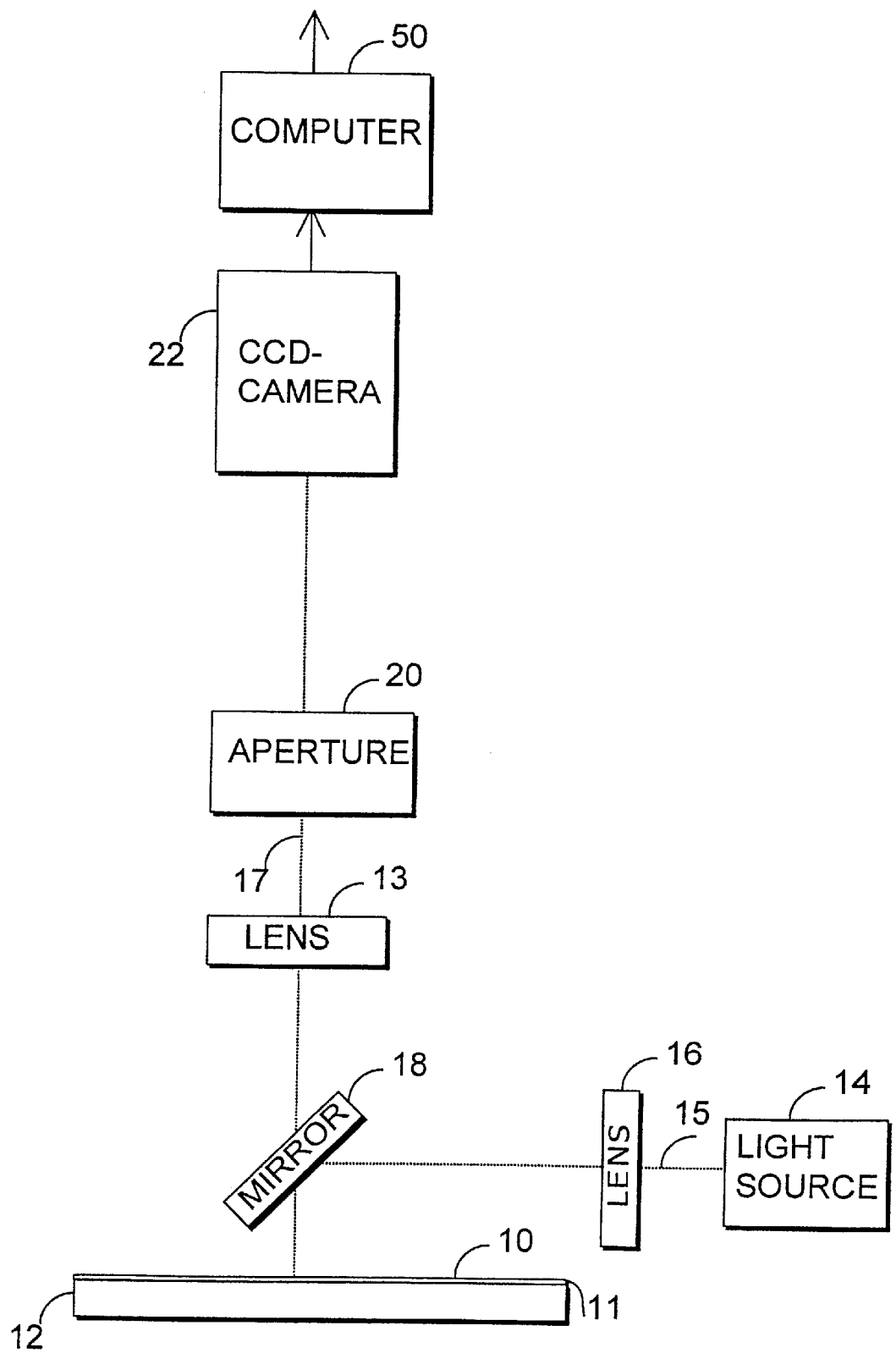
FIG. 1 illustrates a measuring arrangement for measuring micro surface properties of the paper or paperboard surface.

Now we will describe the solution according to the invention more closely with reference to FIG. 1. The measuring arrangement comprises paper or paperboard as a sample 11, an optical power source 14 for emitting optical radiation 15 onto the paper or paperboard 11 surface 10 and a collimating optical block 16 for collimating the radiation 15 and a mirror 18 for projecting the collimated radiation 15 onto the sample 11 surface substantially parallel with the surface normal of the sample 11. The solution according to the invention allows slight deviation in the direction of the surface normal, e.g. less than 10 degrees. The mirror used in the inventive solution is a partially permeable mirror 18, e.g. a semi-permeable mirror. The paper or paperboard 11 is preferably placed on an even and firm base 12. The measuring arrangement further comprises an aperture 20 of the desired size. Reflected optical radiation 17 consists of specular reflection and part of the scattered optical radiation. When gloss is measured, the aperture 20 limits the incidence angle of radiation to the camera 22 (this will be described more closely in FIG. 3), i.e. limits the access of scattered radiation onto the camera's 22 detector surface. When roughness is measured, the size of the aperture 20 determines the depth of focus (described more closely in connection with FIG. 5). The measuring arrangement also preferably comprises a computer 50 for computer-based image analysis. The collimating optical block 16 and the imaging optical block 13 comprise at least one lens. The imaging optical block 13 is dimensioned so that details of the paper or paperboard 11 surface 10 in the order of micrometers can be distinguished from the image which is formed on the camera's 22 detector surface, which allows measurement of micro surface properties from the surface 10. The order of the imaging optical block 13, the partially permeable mirror 18 and the aperture 20 of the desired size in the route of the reflected optical radiation 17 is not relevant to the invention, i.e. the order may differ from what has been shown in FIG. 1. The camera 22 is e.g. a CCD camera (Charge Coupled Device) which is known per se and the detector surface of which is a matrix consisting of pixels. The image produced by the camera is preferably processed in the shades of gray in the computer 50, and therefore the camera may be a black and white camera.

The optical power source 14 preferably has a wide enough optical band, which allows to avoid any problems caused by the speckle phenomenon. The speckle phenomenon is typical particularly in monochromatic optical sources of radiation. The wider the band of optical radiation, the less the speckle images interfere with the measuring according to the invention. Optical power sources that can be applied in the solution according to the invention include glow filament lamps and gas discharge lamps as well as semi conductive components, such as the xenon lamp or the LED (Light Emitting Diode). In this application optical radiation refers to radiation which ranges from ultraviolet to infrared in the optical band (corresponds approximately to the range of 40 nm to 1 mm). The optical radiation 19 received by the camera 22 forms an image onto the pixels of its detector surface. The information included in the image is used for determining a micro surface property of the paper or paperboard 11 surface 10.

Figure 2:
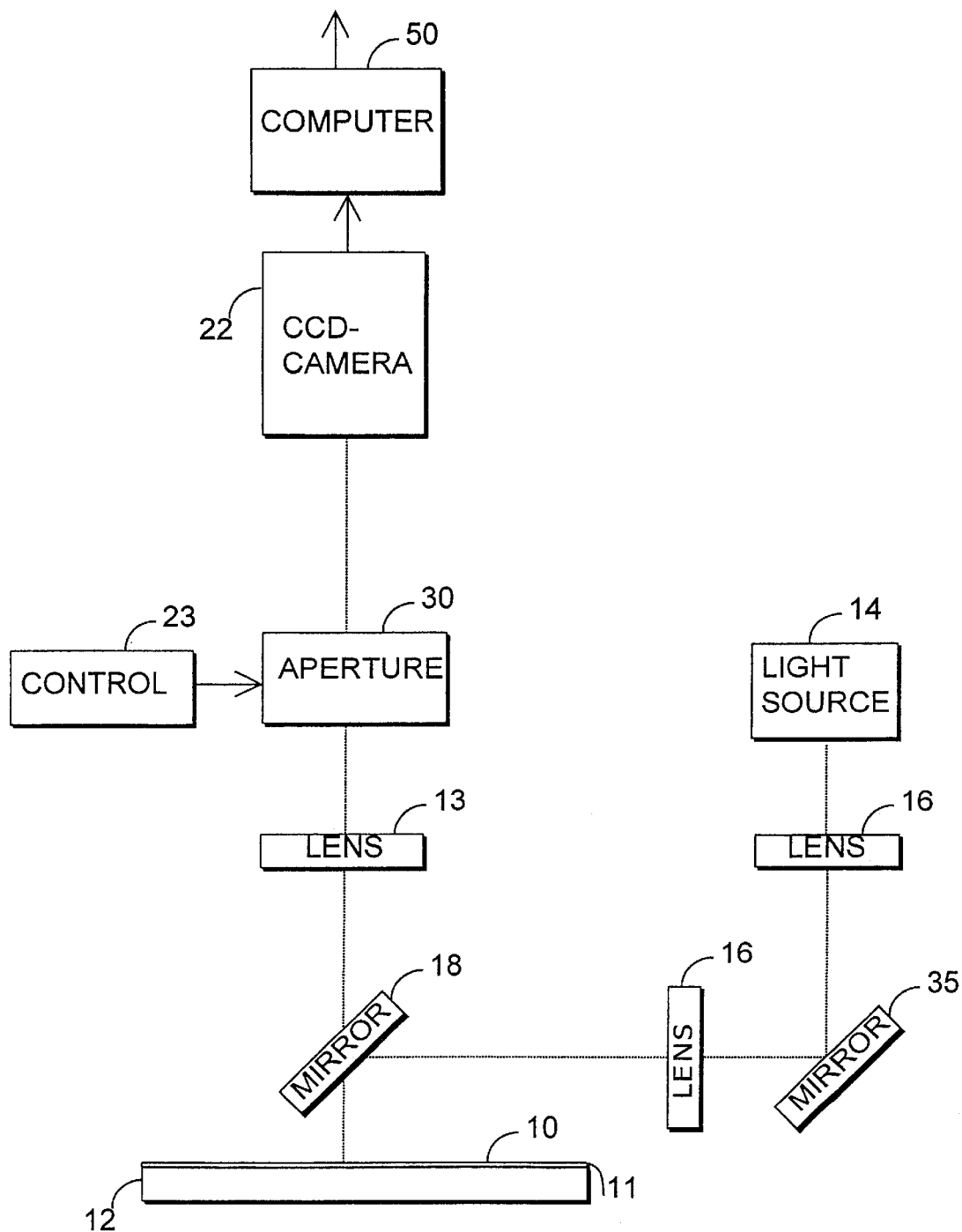
FIG. 2 illustrates a measuring arrangement for measuring gloss of the paper or paperboard surface.

FIG. 2 illustrates a measuring arrangement according to the invention for determining micro gloss of the paper 11 or paperboard 11 surface 10. This measuring arrangement comprises the same parts as the measuring arrangement shown in FIG. 1, but the size of the aperture 30 can be adjusted with a control block 23. A further difference is that the radiation emitted by the optical radiation source 14 is projected onto the paper or paperboard 11 surface using a mirror 35. For this reason the collimating optical block is divided into two lenses 16 in FIG. 5. By changing the size of the aperture 30 the incidence angle of the radiation to the camera's detector surface can be adjusted. This allows to control the amount of scattered radiation to be included in each measurement.

Figure 3:
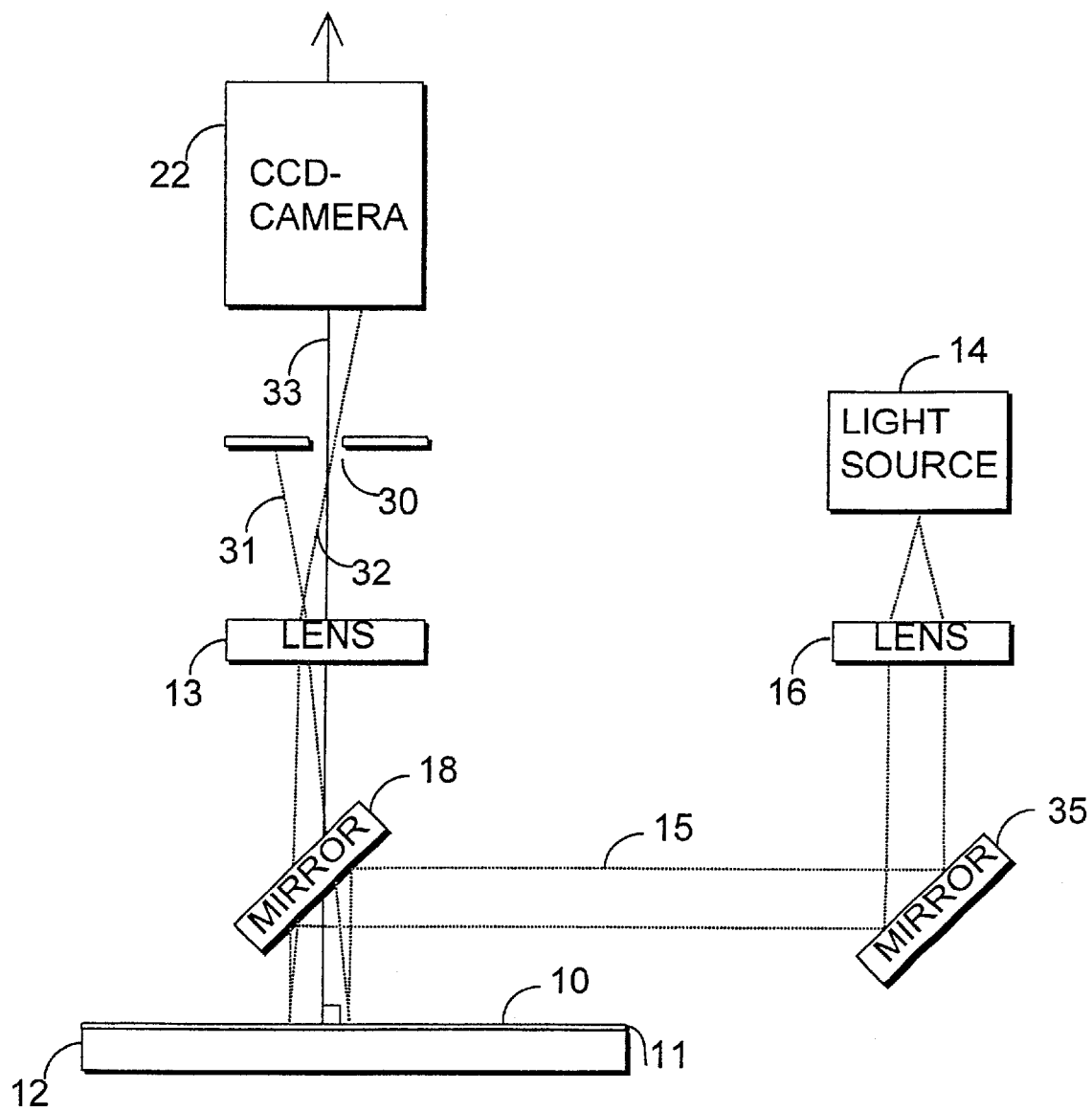
FIG. 3 illustrates dependency between an optical aperture and optical radiation reflected from the surface.

The surface 10 of glossy paper 11 or paperboard 11 has a high specular reflection. The less glossy the paper 11 or paperboard 11 surface 10, the more the surface 10 scatters optical radiation. As illustrated in FIG. 3, optical radiation 31 scattered from the surface 10 passes at an oblique angle with respect to the normal 33 of the surface and does not hit the aperture 30, whereas the optical radiation 32 specular reflected from the surface 10 enters the aperture 30 almost perpendicularly and passes through the aperture 30 to the camera 22. When a larger aperture 30 is used, the ray 31 can also pass to the camera's detector surface. A very small aperture 30 substantially allows only specular reflected radiation 32 to the camera's 22 detector surface. Thus the glossier the paper 11 or paperboard 11 surface 10, the larger the amount of optical radiation allowed to the camera's 22 detector surface is. The glossier the paper, the larger the number of pixels is that have received specular reflected rays. The ratio of the scattered radiation (dark pixels or pixels with low intensity) to the specular reflected radiation (bright pixels or pixels with high intensity) is essential to the measurement of gloss. In the gloss measurement the aperture 30 is preferably located at the focal point of the optical block 13, in which case the aperture can be very small. In that case the camera 22 needs to be provided with an objective for forming an image of the paper or paperboard 11 surface onto the camera's 22 detector surface.

When a single pixel distinguishes a surface area unit of e.g. 3 micrometers * 3 micrometers from the surface 10, the micro surface areas can be detected one by one according to the solution of the invention and the gloss of each surface area unit can be determined as micro gloss. Instead of one pixel, the surface 10 image can be examined using a pixel set. The total measurement area of micro gloss may be e.g. 2.6 mm * 2 mm and the resolution 3 micrometers. This resolution is the micro area of the surface 10 distinguished/separated by a single pixel or a known pixel set. Typical pixel sets include a 5×5 pixel matrix or a cross-shaped pixel set including 5 or 9 pixels, for example.

Images are taken from the same surface 10 area of the paper or paperboard 11 surface 10 preferably with different aperture sizes using an adjustable aperture 30. The images are analysed e.g. with computer-based image analysis where intensity differences of images taken from the same surface 10 area using apertures of different sizes are compared and gloss of the paper 11 or paperboard 11 surface 10 is determined on the basis of this comparison. Comparison of intensity differences is carried out pixel by pixel, i.e. the intensity obtained with a single pixel or a pixel set of an image taken with a certain sized aperture is compared with the intensity value obtained with the same pixel or a known pixel set of an image produced with a different-sized aperture. This allows to determine with the accuracy of pixel or pixel set how each dot-sized surface area of the surface 10 to be imaged has reflected optical radiation 15. In other words, the gloss of micrometric areas, i.e. micro gloss, can be determined with a computer-based image analysis program.

In the gloss measurement, gloss can also be estimated on the basis of an image produced with one aperture size only, but at the expense of accuracy. In that case gloss is determined from the intensity of a single pixel or a known pixel set of t least one image produced using one aperture size. This is preferably performed on the whole imaged area, which yields information on the gloss of the whole imaged area with the accuracy of micrometers. When good accuracy is needed in the measurement of gloss, e.g. when the paper surface is very uniform and glossy, the gloss of such a paper surface has to be determined using images produced with more than one aperture size.

Figure 4:
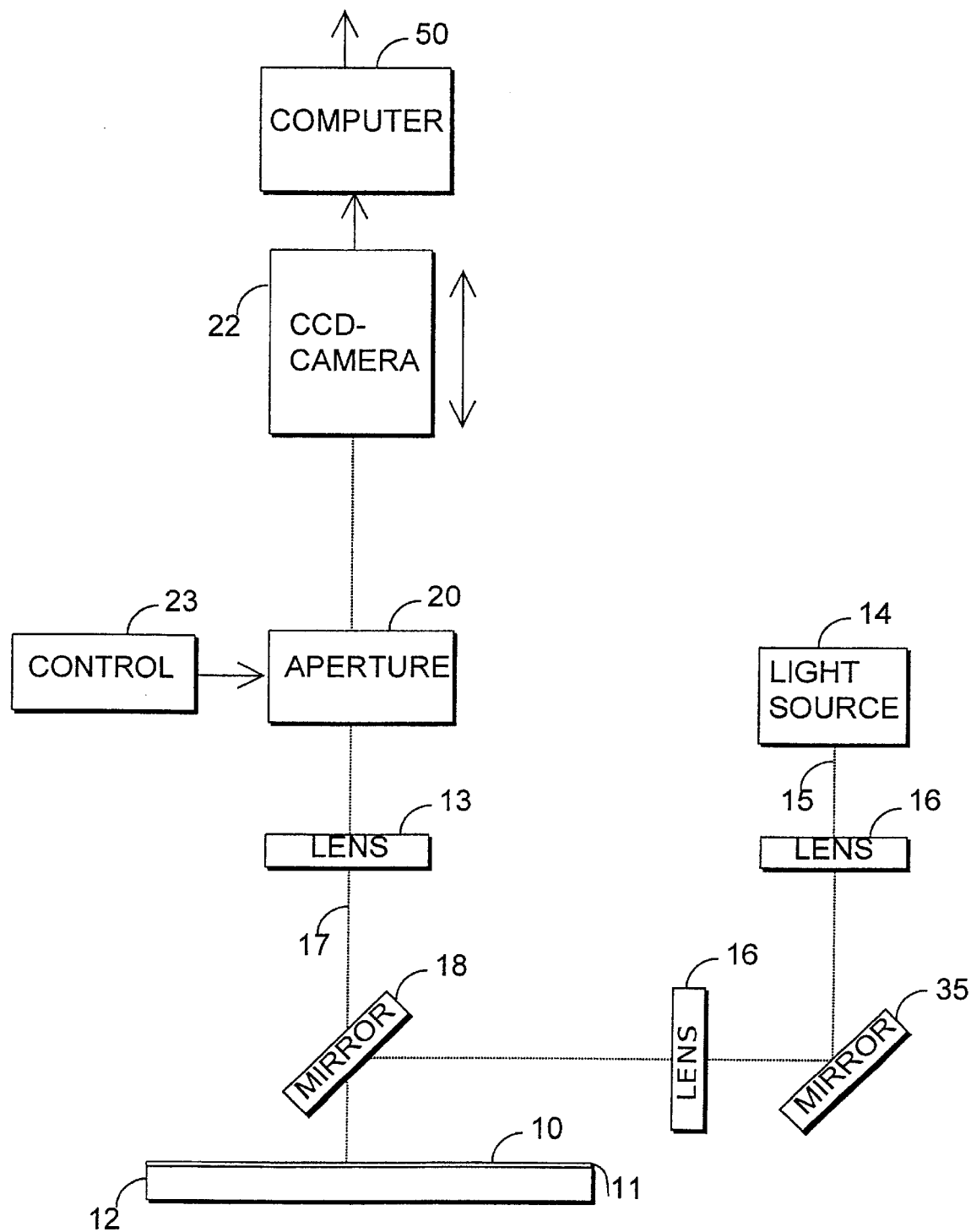
FIG. 4 illustrates a measuring arrangement for measuring roughness of the paper or paperboard surface.

FIG. 4 illustrates a measuring arrangement according to the invention for determining roughness of the paper or paperboard 11 surface 10. This measuring arrangement comprises the same parts as the arrangement shown in FIG. 1. However, he focal point of the optical block 13 that forms image on the camera's 22 detector surface can be moved in depth, which at its simplest is implemented by moving the camera 22 up and down. A further difference is that the radiation emitted by the optical radiation source 14 is projected onto the paper or paperboard 11 surface using a mirror 35. For this reason the collimating optical bloc is divided into two lenses 16 in FIG. 2. The paper or paperboard 11 is preferably placed on an even and firm base 12. According to the method, the paper or paperboard 11 surface 10 is illuminated with the optical power source 14 via the collimating optical block 16 and partially via the permeable mirror 18. The collimating optical block 16 collimates the radiation 15 and the semi-permeable mirror 18 projects the radiation 15 onto the paper 11 or paperboard 11 surface 10 substantially parallel with the surface normal of the paper 11 or paperboard 11. Optical radiation 17 reflected (specular reflection and scattering radiation) from the paper 11 or paperboard 11 surface 10 due to the radiation 15 passes via the semi-permeable mirror 18 and the imaging optical block 13 into an aperture 20 of the desired size which lets at least part of the optical radiation 17 reflected from the surface 10 to the camera 22. Thus an image of the surface is formed on the camera's 22 detector surface in the same way as in the measurement of micro gloss. When roughness is measured, a large aperture provides accurate depth separation. The size of the aperture can be adjusted according to the need with a control block 23. In this measurement it is also important that the imaging optics allows to distinguish micrometric details from the surface 10 image (one pixel corresponds to an area of 3 $\mu$m×3 $\mu$m, for example).

Figure 5:
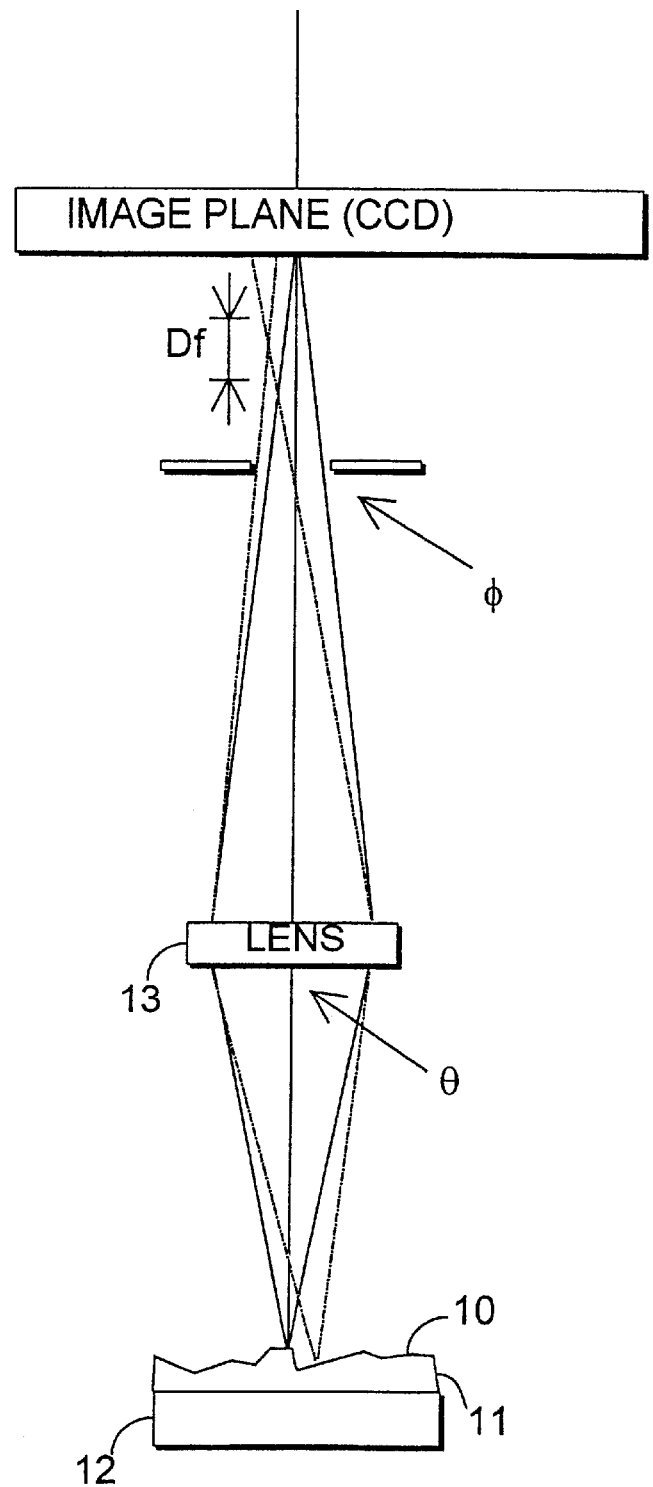
FIG. 5 illustrates determination of the depth of focus.

Because depth separation is important to the measuring method of micro roughness, the method employs as large an aperture as possible. A large aperture has a low depth of focus, for which reason a large aperture is advantageous in the measurement of roughness. The average depth of focus is determined e.g. according to the following formulae (factors of the formulae are shown in FIG. 5):

$$Df = \frac{\lambda}{(2NA)^2}$$

$$NA = n\sin\theta = \frac{\phi}{2f}$$

$$Df = \frac{\lambda}{4\phi^2/4f^2} = \frac{\lambda f^2}{\phi^2}$$

The factors of the formulae are: $\lambda$=wave length of optical radiation, NA=numerical aperture, n=refractive index of medium, $\theta$=angle at which optical radiation enters the objective, $\phi$=diameter of aperture and f=focal distance of lens. As can be seen from the formula, the depth of focus is a function of the square of the diameter's inverse and thus a large aperture enables accurate measuring of roughness.

In the inventive solution shown in FIG. 4 the optical distance between the camera 22 and the paper or paperboard 11 surface 10 is changed instead of moving the camera 22 and images are produced at different optical distances. Thus the camera's 22 detector surface can be focused according to the height variations of roughness. The optical distance between the camera 22 and the paper or paperboard 11 surface 10 can be changed e.g. by using permeable sheets of different thicknesses in the route of the optical radiation 17 reflected from the surface 10, which can be implemented e.g. with a rotatable disc 60 of FIGS. 6A and 6B which consists of sectors 61 to 63 of different thicknesses. Naturally the disc 60 has to be made of a material which has a good permeability of optical radiation and is optically flawless.

Figure 6A:
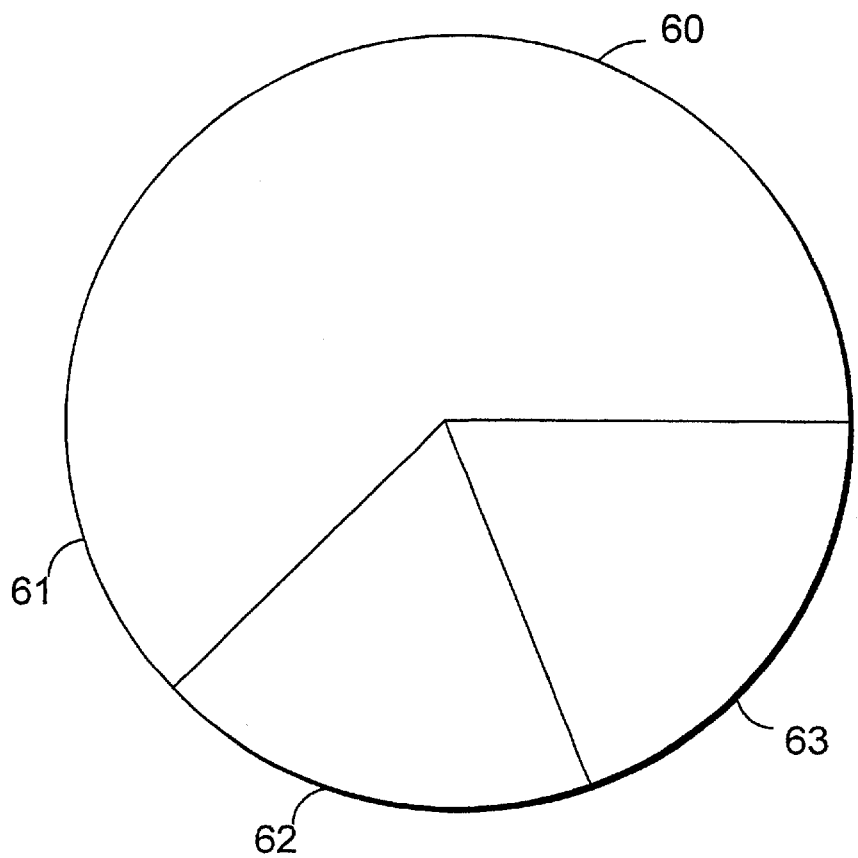
FIG. 6A is a top view of a rotatable disc.
Figure 6B:
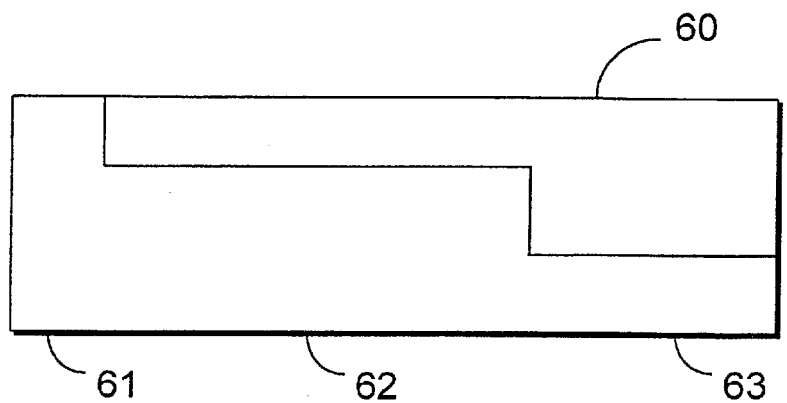
FIG. 6B is a perpendicular side view of a rotatable disc.

The material may be e.g. glass or plastic but other optical materials are also suitable. FIG. 6A is a top view of the disc 60 and FIG. 6B is a perpendicular side view of the disc 60. The images are analysed using e.g. computer-based image analysis where changes in the intensity of the pixels of the images formed with different depths of focus are compared, which allows to form a height map of the paper 11 or paperboard 11 surface 10. The measurement is based on that fact that the intensity of each pixel is maximal when the image falling on the pixel is focused. The intensity of non-focused pixels decreases as the focusing becomes less accurate. In the image analysis intensity maxims or image edges are searched for using an image processing program. This method according to the second preferred embodiment of the invention allows to determine the roughness of paper 11 or paperboard 11 surface 10 even with the accuracy of micrometers. However, the accuracy depends on the size of the aperture 20.

Now we will describe in greater detail the determination of roughness on the basis of the images taken. A desired number of images are taken e.g. using standard differences in the depth of focus. To improve quality and to decrease interference, several images can be taken using the same depth of focus and by calculating the average of the images digitized by the computer. Then the difference in the intensity of pixels or a group of pixels is determined between successive images taken using different depths of focus. After this, a surface roughness map or another result describing roughness is formed with a computer utilizing the information that the intensity of pixels or a pixel set is at its highest at the focus. It is not necessary to process the whole imaged area formed on the camera's detector surface in this way, but a representative sample of the imaged area is sufficient. Such an image processing algorithm has been applied to roughness measurements of metal surfaces in Steurer, J., Giebel, H., and Altner, W.: Ein lichtmikroskopisches Verfahren zur zweieinhalbdimensionalen Auswertung von Oberflächen, In Proc. 8. DAGM-Symp. Mustererkennung, 1986, Informatik Fachberichte 125, edited by G. Hartmann, pp. 66–70, Springer, Berlin, which is incorporated herein by reference.

Figure 7:
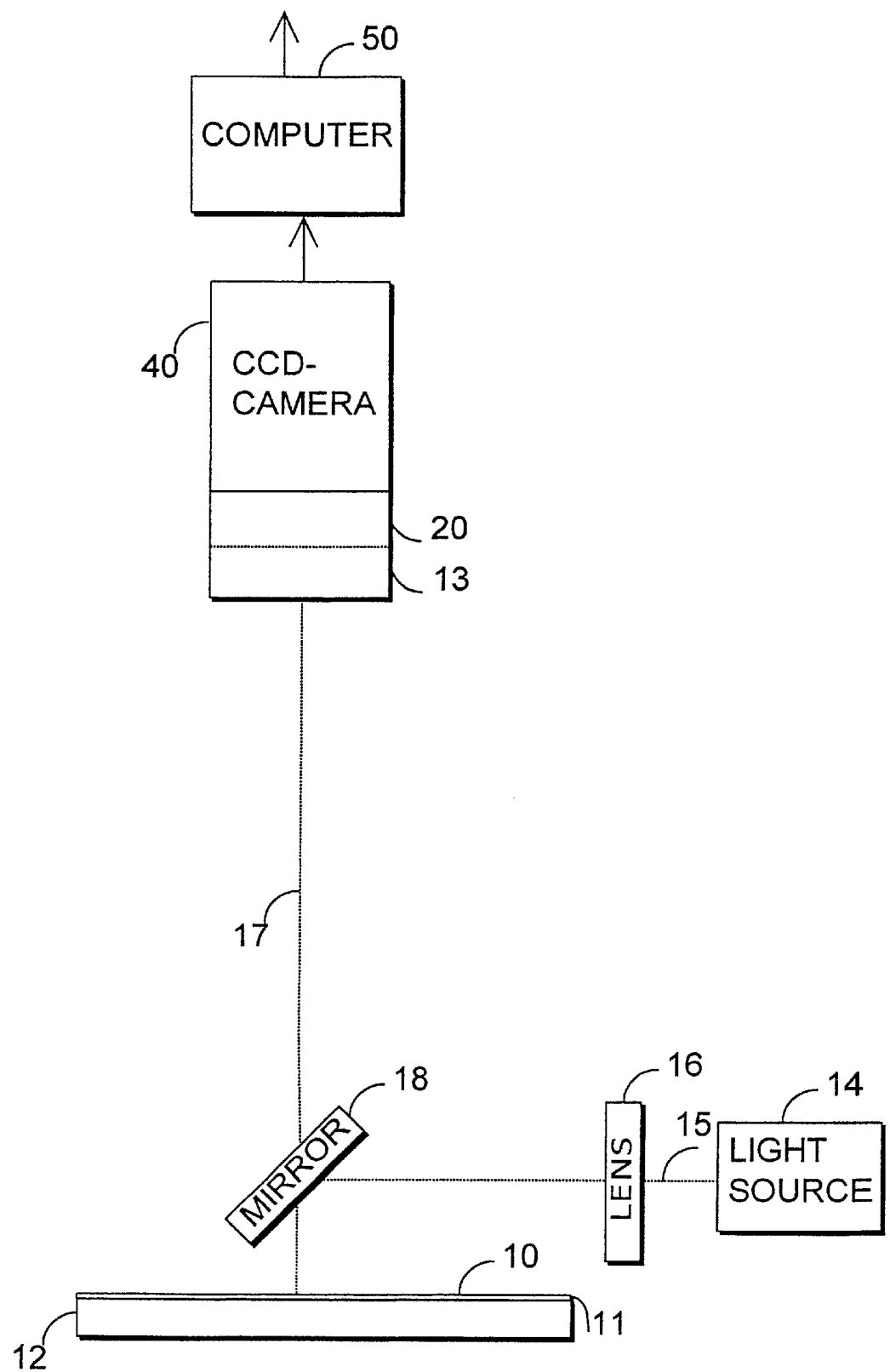
FIG. 7 illustrates a measuring arrangement for determining micro surface properties of the paper or paperboard surface.

FIG. 7 illustrates a measuring arrangement according to the invention which corresponds to the measuring arrangement shown in FIG. 1, except that the imaging optical block 13 and the aperture 20 of the desired size are integrated into the camera 40. The measuring arrangement can be implemented as described above both in the first and in the second embodiment of the invention.

In the solution according to the invention both gloss and roughness can be measured successively with the same measuring arrangement or determined even from the same images. Measurements of roughness and/or gloss can be used for controlling the papermaking process of a paper machine to maintain the desired quality of the paper/paperboard to be manufactured. Information on a surface property or control corrections due to surface property measurements can be fed into the control arrangement of a paper machine either automatically or manually. The solution according to the invention is also applicable to continuous on-line measuring of the paper 11 or paperboard 11.

Even though the invention has been described with reference to the embodiment according to the accompanying drawings, it is obvious that the invention is not restricted thereto, but may be modified in several ways within the scope of the inventive concept disclosed in the appended claims.

What is claimed is:

1. A method of determining a surface property of paper or paperboard, the method comprising
    illuminating the paper or paperboard surface with collimated light substantially parallel with the normal of the paper or paperboard surface;
    imaging the illuminated paper or paperboard surface onto the pixels of a camera's detector surface;
    controlling the reflected optical radiation with an aperture of the desired size before the camera;
    producing an image of the paper or paperboard surface onto the pixels of the camera's detector surface by means of the reflected optical radiation, each of the pixels imaging a surface area in the order of micrometers of the paper or paperboard;
    focusing the image of the paper or paperboard surface in depth at different distances by changing the optical distance between the camera and the paper or paperboard surface and
    measuring at least the gloss of the paper or paperboard surface at different optical distances on the basis of the intensity of the pixels on the camera's detector surface.

2. A method according to claim 1, further comprising measuring roughness of paper or paperboard also on the basis of the intensity of the pixels on the camera's detector surface.

3. A method according to claim 2, further comprising determining by the aperture the depth of focus of imaging in the measurement of roughness.

4. A method according to claim 2, wherein the measurement of roughness comprises the following steps:
    producing images with the camera using different depths of focus;
    determining a pixel-specific or a pixel set-specific difference in the intensity between successive images produced using different depths of focus;
    determining surface height variations utilizing the information that the intensity of a pixel or a pixel set is at its highest at the focus, and
    determining the roughness of paper or paperboard (11) from the surface height variations.

5. A method according to claim 4, further comprising producing several images using the same depth of focus and the average of digitized images is calculated to decrease interference.

6. A method according to claim 4, further comprising forming a height map illustrating roughness on the paper or paperboard surface by means of the images produced.

7. A method according to claim 1, further comprising using the aperture for limiting the incidence angles of the reflected optical radiation to the camera's detector surface for measuring gloss.

8. A method according to claim 1, further comprising measuring gloss from the paper or paperboard surface by means of specular reflected and scattered radiation by determining the ratio of the pixels that have received specular reflected rays to the other pixels, the intensity of the specular reflected radiation being higher than the intensity of the scattered radiation.

9. A method according to claim 1, wherein the aperture is adjustable.

10. A method according to claim 1, further comprising projecting illumination onto the paper or paperboard surface through a partially permeable mirror.

11. A method according to claim 1, further comprising comparing the images produced with one another in computer-based image analysis.

12. A method according to claim 1, further comprising determining the printability of paper or paperboard at least for the gloss measurement.

13. A method according to claim 1, further comprising measuring paper or paperboard on-line.

14. A measuring arrangement for determining a surface property of paper or paperboard, the measuring arrangement comprising an optical power source for illuminating the paper or paperboard surface and a camera for producing an image of the illuminated paper or paperboard surface onto the pixels of the camera's detector surface, wherein the measuring arrangement according to the invention comprises:

- a collimating optical block for collimating the optical radiation;
- a partially permeable mirror for projecting the optical radiation onto the paper or paperboard surface substantially parallel with the normal of the paper or paperboard surface;
- an imaging optical block for producing an image of the illuminated paper or paperboard surface onto the pixels of the camera's detector surface by means of the reflected optical radiation; and
- an aperture of the desired size for controlling the reflected optical radiation; and
- the measuring arrangement is arranged to change the optical distance between the camera and the paper or paperboard surface to change the focal point on the paper or paperboard surface, and
- the measuring arrangement is arranged to measure at least gloss of the paper or paperboard surface at different optical distances on the basis of the intensity of the pixels on the camera's detector surface.

15. A measuring arrangement according to claim 14, wherein the measuring arrangement is also arranged to measure roughness of paper or paperboard on the basis of the intensity of the pixels on the camera's detector surface.

16. A measuring arrangement according to claim 15, wherein the aperture is arranged to control the reflected optical radiation by limiting the depth of focus of imaging in the desired manner when roughness is measured.

17. A measuring arrangement according to claim 15, wherein the measuring arrangement is arranged to produce images with different depths of focuses;

determine a pixel-specific or a pixel set-specific difference in the intensity between successive images produced with different depths of focus;

determine surface height variations utilizing the information that the intensity of a pixel or a pixel set is at its highest at the focus, and determine roughness of paper or paperboard from the surface height variations.

18. A measuring arrangement according to claim 17, wherein the measuring arrangement is arranged to produce several images with the same depth of focus and to calculate the average of the digitized images to decrease interference.

19. A measuring arrangement according to claim 17, wherein a computer (50) is arranged to provide a height map on the images.

20. A measuring arrangement according to claim 14, wherein the aperture is arranged to control the reflected optical radiation by limiting the incidence angles of the reflected optical radiation to the camera's detector surface to improve the gloss measurement.

21. A measuring arrangement according to claim 14, wherein the measuring arrangement comprises a control block for adjusting the aperture.

22. A measuring arrangement according to claim 14, wherein the measuring arrangement is arranged to measure gloss from the ratio of the specular reflected radiation to the scattered radiation by determining the number of pixels that have received specular reflected rays in relation to the number of other pixels, the intensity of the specular reflected radiation being higher than the intensity of the scattered radiation.

23. A measuring arrangement according to claim 14, wherein the camera is a CCD camera.

24. A measuring arrangement according to claim 14, wherein the measuring arrangement comprises an image processing device which is arranged to use an image analysis program to determine a surface property.

25. A measuring arrangement according to claim 14, wherein the measuring arrangement is arranged to determine the printability of paper or paperboard by means of at least one micro surface property.

26. A measuring arrangement according to claim 14, wherein the measuring arrangement is arranged to measure paper or paperboard on-line.

* * * * *